(12) United States Patent
Berns et al.

(10) Patent No.: US 11,698,520 B2
(45) Date of Patent: Jul. 11, 2023

(54) SYSTEMS AND METHODS FOR LASER SCISSORS AND TWEEZERS WITH A QUANTITATIVE PHASE MICROSCOPE (QPM)

(71) Applicant: The Regents of the University of California, Oakland, CA (US)

(72) Inventors: Michael W. Berns, Irvine, CA (US); Nicole Wakida, Irvine, CA (US); Daryl Preece, Irvine, CA (US); Toyohiko Yamauchi, Irvine, CA (US); Pegah Pouladian, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 7 days.

(21) Appl. No.: 17/468,223

(22) Filed: Sep. 7, 2021

(65) Prior Publication Data

US 2022/0107488 A1   Apr. 7, 2022

Related U.S. Application Data

(60) Provisional application No. 63/075,586, filed on Sep. 8, 2020.

(51) Int. Cl.
    *G01N 21/64*     (2006.01)
    *G02B 21/32*     (2006.01)
    *G01N 33/483*    (2006.01)

(52) U.S. Cl.
    CPC ......... *G02B 21/32* (2013.01); *G01N 21/6402* (2013.01); *G01N 21/6458* (2013.01); *G01N 33/4833* (2013.01)

(58) Field of Classification Search
    CPC ........ G02B 21/32; G02B 21/00; G02B 21/14; G02B 21/36; G01N 21/6402; G01N 21/6458; G01N 33/4833; G01N 21/17; G01N 21/41; G01N 21/45; G21K 1/00
    See application file for complete search history.

(56) References Cited

U.S. PATENT DOCUMENTS

2018/0341098 A1* 11/2018 Anvari ................... G02B 21/26
2022/0107488 A1*  4/2022 Berns ................. G01N 21/6458

OTHER PUBLICATIONS

Yu et al., "Digital holographic microscopy for quantitative cell dynamic evaluation during laser microsurgery," Optics Express, vol. 17, No. 14, pp. 12031-12038. (Year: 2009).*

* cited by examiner

*Primary Examiner* — Kiho Kim
(74) *Attorney, Agent, or Firm* — John Teresinski; Stites & Harbison, PLLC

(57) ABSTRACT

Systems and methods are provided for Quantitative Phase Microscopes (QPM) having laser systems including one or more of laser scissors and laser tweezers. In one embodiment, the system includes one or more structural elements, such as a stage and dichroic plate for operation of a QPM with laser scissors/tweezers. Another embodiment is directed to a method of operating a QPM system having laser scissors/tweezers. One or more solutions are provided for biodmedical applications of a QPM system including simulation and analysis of trauma on cellular structures and organelles. Processes are also provided for simulation and analysis of traumatic injury, including imaging and analysis of astrocytes.

20 Claims, 8 Drawing Sheets

SYSTEMS AND METHODS FOR LASER SCISSORS AND TWEEZERS WITH A QUANTITATIVE PHASE MICROSCOPE (QPM)

CROSS REFERENCE TO RELATED APPLICATION

This application claims priority to U.S. provisional application No. 63/075,586 titled SYSTEMS AND METHODS FOR LASER SCISSORS AND TWEEZERS WITH A QUANTITATIVE PHASE MICROSCOPE (QPM) filed on Sep. 8, 2020, the content of which is expressly incorporated by reference in its entirety.

STATEMENT OF GOVERNMENT SUPPORT

This invention was made with Government support under Grant No. FA9550-20-1-0052 awarded by Air Force Office for Scientific Research (AFSOR). The Government has certain rights in the invention.

FIELD

The present disclosure generally relates to use of laser technologies, including laser scissors and tweezers, and quantitative phase imaging (QPI), and in particular a quantitative phase microscope (QPM) for biomedical applications.

BACKGROUND

Conventional microscope systems have been developed using laser systems to study and manipulate cells. Existing systems use conventional microscope approaches such as, phase contrast, bright field or fluorescence microscopy. One example, U.S. Pat. No. 9,321,990 titled Systems and Methods for Identifying and Disrupting Cellular Organelles, describes use of laser systems to manipulate cell organelles that exhibited fluorescence due to an applied chromophore (or genetically programmed fluorescence). In a fluorescence microscope approach, certain compounds are illuminated with high energy light. The compounds emit light of a lower frequency which can be detected. The emitted fluorescence can characterize fluorescence image, based on their chemical makeup.

There exists a desire for imaging methods to study cellular trauma. Based on the Centers for Disease Control and Prevention, traumatic brain injury happens when an external force is applied to the head and interferes with the normal function of the brain. From 2006 to 2014, the rate of TBI-related emergency visits, hospitalizations or deaths had increased by more than 50%, which were approximately 2.87 million.

TBI is known as the most common disease that causes death and physical impairment in youth. Based on the level of consciousness, it is categorized as mild, moderate, or severe. Side effects of this malady can vary from a full neurological recovery along with/without short-term memory and concentration impairments, to death. It is important to note that the severe damage, which is the chief cause of death after TBI, is not when the mentioned force is applied (primary injury), but it happens afterwards (secondary injury).

Studies have shown that the secondary injury is characterized by an increase in intracranial pressure which is followed by a decrease in cerebral perfusion and ischaemia (Ghajar, 2000). Several treatments have been tested to prevent the secondary injury; however, none of them have been proven to be successful, leading to the conclusion that the mechanism of the disease is still not completely clear at the cellular level (Ghajar, 33 2000).

Various models have been proposed to simulate traumatic brain injury. They can be categorized as acceleration models of TBI, compression models of TBI, repetitive models of mild TBI, and blast models of TBI. For the acceleration models, to simulate the stress, the acceleration is applied to the brain of the animal, like a rat. However, the acceleration must be amplified since the animals' brain is smaller. This has made these models challenging as this high acceleration must be exerted without causing any deformations to the skull of the animal. (Finan, 2019). In Compression models, the simulation is comprised of controlled cortical impact injury (CCI) and fluid percussion injury (FPI). For CCI, a controllable piston is used to rapidly induce the injury to the brain (Osier and Dixon, 2016). For FPI, a fluid is injected through the brain in pulses to make a transient deformation (Carbonell et al., 1998). In both of these methods, the injury is induced to the open skull which is different from what actually happens in TBI; however, they have shown similarity in results with the clinical pathology (Finan, 2019). Various methods have been proposed for repetitive mild TBI. For instance, (Kane et al., 2012) by modifying the Marmarou weight drop method, have been able to anesthetize unrestrained mice by impacting the brain repeatedly, which is a close simulation to the injury which is caused to the human brain during concussion TBI by the increase in blast-induced TBI (bTBI) caused by improvised explosive devices, impacting the brain directly, and also indirectly in the thorax, blast models of TBIs have been proposed to study its effects (Finan, 2019). Different methods have modeled TBI. As one method, laser-induced Shockwaves (LIS) have shown to be an effective way to simulate the shockwave in vivo (Nakagawa et al., 2008) and in vitro (Selfridge et al., 2015). However, the precise mechanism of the primary bTBI is still not completely understood (Nakagawa et al., 2011). Previously, LIS has been applied on mouse brains, in vivo, by placing the mouse in a certain position and applying shockwaves on the skin surface over the intact brain. The brain tissue was then excised for further analysis. Even though this model has been represented as TBI, it was not possible to study the cellular changes during and right after the injury.

To further investigate the effectiveness of LIS, the response of hippocampal brain cells to injuries caused by LIS and sub-axotomy have demonstrated similar responses to the two different injuries in terms of cytoskeletal dynamics. Although a wavelet algorithm has been used to quantitatively measure the induced damage to the cells, precise direct quantitative measurement of the shock wave damage has not been possible (Selfridge et al., 2015).

When an injury occurs to the brain, neural and non-neural cells in the brain interact with each other to maintain the brain's normal function. In this regard, astrocytes, the most numerous cells in the CNS, play a crucial role to maintain the stable equilibrium between ions, maintain homeostasis of water and blood flow, recycle the neurotransmitters and supply the nutrition that cells need to remain healthy.

There exists a need and desire for improved imaging and improved study and manipulation of nerve cells and other cells in the nervous system such as astrocytes and other astroglial cell types. There also exists a need for improved methods to analyze cellular trauma and repair in TBI as well as in a significant number of other disease systems such as Alzheimer's, Parkinson's, and Huntington's Disease, just to name a few.

BRIEF SUMMARY OF THE EMBODIMENTS

Disclosed and described herein are systems, methods and configurations for a quantitative phase microscope (QPM) system. In one embodiment, a QPM system includes a structural unit configured to retain a sample, and a laser system configured to perform at least one of a laser scissor and laser tweezer operation on the sample. The QPM system also includes a quantitative phase microscope (QPM) configured to image the sample.

In one embodiment, the structural unit includes a dichroic plate, wherein the dichroic place is transparent to the laser system and reflective to output of the QPM.

In one embodiment, the laser system is configured to output a shockwave output to the sample to simulate trauma in the sample.

In one embodiment, the QPM system is configured to simulate and analyze trauma on at least one of cellular structures and organelles.

In one embodiment, the system includes a fluorescent microscope element configured to localize and quantify at least one molecular component of the sample during and after shockwave injury.

In one embodiment, the laser system is configured to image and analyze at least one astrocyte of the sample.

In one embodiment, the laser system is configured to perform both a laser scissor operation and laser tweezer operation to analyze the sample.

In one embodiment, the QPM is configured to measure at least one of recovery of the sample, intracellular dynamics, and quantitative changes in membrane thickness in real time.

In one embodiment, the system also includes a controller configured to control the laser system, and control the QPM, wherein the controller controls the QPM to image the sample.

In one embodiment, the controller is configured to control the QPM to determine optical path-length of the sample, measure organelle movement in a cell, and quantify cell dynamics including membrane motility.

Another embodiment is directed to a method for operation by a quantitative phase modulated (QPM) system. The method includes controlling, by a controller, a laser system configured to perform at least one of a laser scissor and laser tweezer operation on a sample, and controlling, by the controller, imaging by a quantitative phase microscope (QPM) to image the sample.

In one embodiment, the laser system is configured to output a shockwave output to the sample to simulate trauma in the sample.

In one embodiment, the laser system is configured to simulate and analyze trauma on at least one of cellular structures and organelles.

In one embodiment, the method also includes controlling a fluorescent microscope element to localize and quantify at least one molecular component of the sample during and after shockwave injury.

In one embodiment, the method includes controlling the laser system to image and analyze at least one astrocyte of the sample.

In one embodiment, the method also includes performing both a laser scissor operation and laser tweezer operation to analyze the sample.

In one embodiment, the method also includes controlling the QPM to measure at least one of recovery of the sample, intracellular dynamics, and quantitative changes in membrane thickness in real time.

In one embodiment, the method also includes controlling the QPM to determine optical path-length of the sample, measure organelle movement in a cell, and quantify cell dynamics including membrane motility.

In one embodiment, the method also includes controlling the QPM to measure repair process in the sample introduced with at least one pharmaceutical.

In one embodiment, imaging a cell includes determining changes in cell thickness and a resolution of intracellular cytoplasmic damage.

Other aspects, features, and techniques will be apparent to one skilled in the relevant art in view of the following detailed description of the embodiments.

BRIEF DESCRIPTION OF THE DRAWINGS

The application file contains at least one drawing executed in color. Copies of this patent or patent application publication with color drawing(s) will be provided by the Office upon request and payment of the necessary fee.

The features, objects, and advantages of the present disclosure will become more apparent from the detailed description set forth below when taken in conjunction with the drawings in which like reference characters identify correspondingly throughout and wherein.

DETAILED DESCRIPTION OF THE EXEMPLARY EMBODIMENTS

Overview and Terminology

Figure 1:
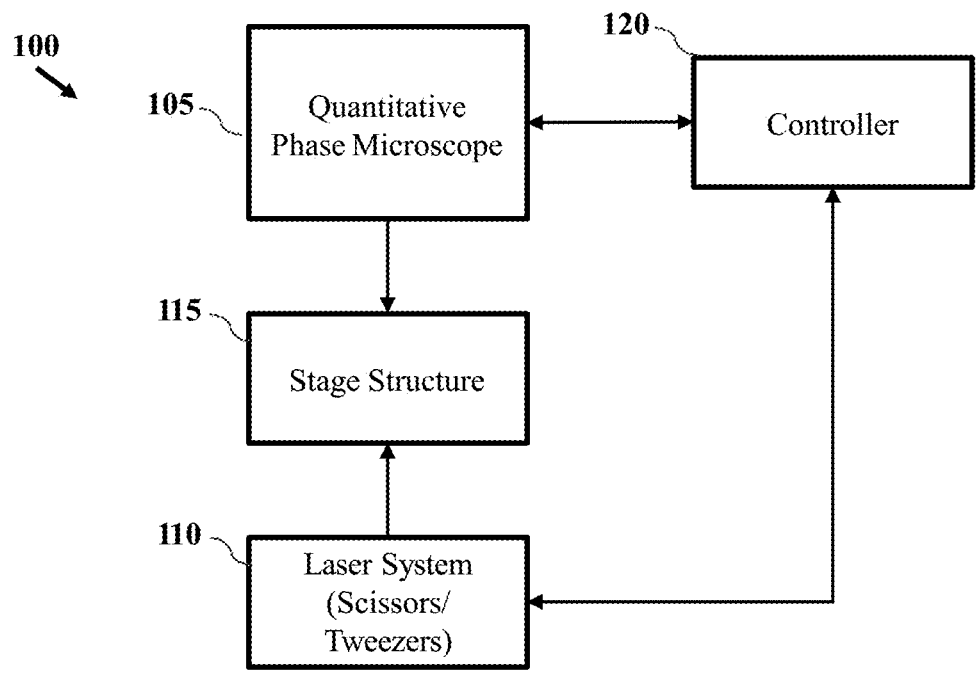
FIG. 1 is a graphical representation of a QPM microscope having a laser system according to one or more embodiments.

One aspect of the disclosure is directed to quantitative phase imaging (QPI) for biomedical applications. In one embodiment, a quantitative phase microscope (QPM) microscope system is provided including a laser system to provide at least one of a laser scissor and laser tweezer. According to embodiments, a QPM microscope can include operations for control of both laser scissor and laser tweezer operations on a sample. The QPM system may be configured for biomedical applications to determine effects of a laser system on one or more cells and cell components. Configurations are provided that integrate laser systems with quantitative phase microscope and for quantitative phase imagining.

By integrating laser technologies with imaging and biochemical techniques, robust systems are provided to study various biological and biochemical processes. As used herein, a quantitative phase microscope may relate to a microscopy method to quantify the phase shift that occurs when light waves pass and/or reflect through an object. A QPM as used herein may relate to quantitative phase contrast microscopy, quantitative phase imaging and quantitative phase contrast.

Laser systems as described herein may relate to components to provide laser scissors, laser tweezers (e.g., optical tweezers, optical traps, etc.) and a combined laser scissors/tweezers configuration. One or more embodiments are directed to structural elements for a QPM and laser system to operate including solutions for introducing high-power laser sources to QPM.

Systems and methods are provided for quantitative phase imaging of samples including fluids and cells. In one embodiment, a process is provided for analyzing cells and cellular organelles during shockwave injury and afterwards. The process and system configurations can enable the measurement of the damage and recovery processes of the cells, intracellular dynamics, and quantitative changes in the membrane thickness in real time. In addition, fluorescent microscopy can be added to the system to localize and quantify changes in calcium and other molecular components during and after shockwave injury, thus providing a unique combination of imaging modalities to study traumatic brain injury (TBI) as well as many other cellular trauma conditions.

According to embodiments, a QPM system includes a structural unit configured to retain a sample, a laser system configured to perform at least one of a laser scissor and laser tweezer operation on the sample, and QPM configured to image the sample. In one embodiment, the system includes a controller configured to control the laser system, and control the QPM. According to another embodiment, the structural unit includes a dichroic plate configured as transparent to the laser system and reflective to the output of the QPM. In one embodiment, the laser system is configured to output a shockwave output to the sample to simulate trauma in the sample. The laser system is configured to simulate and analyze trauma on cellular structures and organelles. In yet another embodiment, the QPM system is configured to image and analyze at least one astrocyte of the sample. The system may be configured to perform one or more processes including controlling, by a controller, a laser system to perform at least one of a laser scissor and laser tweezer operation on a sample. The process may also include controlling imaging by a quantitative phase microscope (QPM) to image the sample.

As used herein, the terms "a" or "an" shall mean one or more than one. The term "plurality" shall mean two or more than two. The term "another" is defined as a second or more. The terms "including" and/or "having" are open ended (e.g., comprising). The term "or" as used herein is to be interpreted as inclusive or meaning any one or any combination. Therefore, "A, B or C" means "any of the following: A; B; C; A and B; A and C; B and C; A, B and C". An exception to this definition will occur only when a combination of elements, functions, steps or acts are in some way inherently mutually exclusive.

Reference throughout this document to "one embodiment," "certain embodiments," "an embodiment," or similar term means that a particular feature, structure, or characteristic described in connection with the embodiment is included in at least one embodiment. Thus, the appearances of such phrases in various places throughout this specification are not necessarily all referring to the same embodiment. Furthermore, the particular features, structures, or characteristics may be combined in any suitable manner on one or more embodiments without limitation.

Exemplary Embodiments

Referring now to the figures, FIG. 1 is a graphical representation of a quantitative phase microscope (QPM) system. System 100 includes a quantitative phase microscope (QPM) 105 and laser system 110 according to one or more embodiments. According to one embodiment, system 100 may be configured to perform operations and imaging of a sample held by stage structure 115. System 110 may include controller 120 configured to control one or more of QPM 105, laser system 110 and stage structure 115. Controller 120 may be configured to control laser system 110 and control QPM 105 to image the sample.

According to one embodiment, QPM 105 may be configured to image a sample, including one or more cellular elements, and the effects on a sample due to laser system 110. QPM 105 may be configured to image based on one or more quantitative phase modulated determinations. QPM 105 may relate to one or more of a reflection and transmission type microscope. In certain embodiments, QPM 105 is a reflection type microscope mounted on a first side of stage structure 115 and laser system 115 is mounted on a second (e.g., opposite) side of stage structure 115. According to one embodiment, QPM 105 may be configured to operate with a reflecting coverslip, wherein the coverslip is at least partially reflecting, and QPM 105 may also include an objective lens located below the sample. According to another embodiment, laser wavelength of QPM 105 must not be the same wavelength as optical range of the QPM but must be transmitted by the coverslip. In addition, a laser of the laser output system must be set up as a triggered single pulse.

According to one embodiment, system 100 is configured to integrate QPM 105 with laser system 110. Stage Structure 115 of system 100 may be a structural unit configured to retain a sample and may include an optically dichroic plate as a substrate for culturing samples. The dichroic plate may be configured as transparent to optical output of the laser system (e.g., laser scissor/tweezers) and reflective to light from QPM 105. System 100 may be configured to mount QPM 115 and laser system to a platform of stage structure 115, the platform including a hole for the sample and mechanical stability in a compact setup. System 100 may be configured to include a laser microscope that will allow manipulation and study of cells from a new perspective.

Laser system 110 can include laser scissors and/or tweezers to manipulate and alter cells, and organelles within a cell, of a sample. As such, laser system 110 may be configured to perform at least one of a laser scissor and laser tweezer operation on the sample. As will be discussed in more detail below, laser system 110 may be configured to shock cells of a sample and QPM 105 may be configured to image impact of the shock on the sample. As used herein, laser tweezers may relate to one or more operations and/or components to hold or move a cell and/or cellular component. Laser tweezer operations may include optical tweezer operations for cellular elements. Laser scissors may relate to optical output to cut one or more of a cellular component and/or cellular membrane. QPM 105 may be configured to measure the increased migratory forces associated with activated cells. These kinds of measurements are difficult or not possible using other technologies.

According to one embodiment, laser system 110 may be integrated above or below stage structure 115. In certain configurations, laser system 110 may be integrated with QPM 105. In one embodiment, laser system 100 is configured to output optical signals and lasers from below stage structure 115. Stage structure 115 may be configured to include a frame and/or stand to raise and lower QPM 105 relative a table surface of stage structure 115 and activate lasers from below. Laser system may be configured to output short pulsed lasers for the scissors on the order of nanosecond (ns) to femtosecond (fs), and wavelengths variable from the ultraviolet (UV) (e.g., ~260 nm) to near infrared (IR) (e.g., ~1.2 microns). Laser system 110 may include components to provide laser or optical scissors configured to alter either the whole cells, or individual structures within cells. The structure of cells in a sample may be imaged based on standard fluorescence, fluorescence resonance energy transfer (FRET), multi-photon imaging, two photon imaging, etc. Components of laser system 110, such as laser tweezers may be integrated with system 100 using one or more lasers. The lasers may operate in continuous wave mode at wavelength from the green to near IR (1.2 microns). Laser output prior to entering the QPM microscope may be 25 milliwatt (mw) to ~2 watt. Laser system 110 may output a trapping beam fractioned into several beams or very rapidly scanned to represent multiple beams using a variety of different optical methods.

According to one embodiment, laser system 110 may also be configured to output optical pulses to output a shockwave to the sample to simulate trauma in the sample. Laser system 110 may also be configured to simulate and analyze trauma on cellular structures and organelles of the sample. Shocking samples may be beneficial for simulating trauma on samples, such as traumatic brain injury (TBI). System 100 may be configured to image and analyze at least one astrocyte of the sample in response to a shockwave generated by the laser system.

System 100 may include controller 120 to perform one or more measurements and/or tests on a sample. Controller 120 may be configured to control laser system 110 and control QPM 105. Testing may include time-lapse imaging, cell tracking, cell differentiation, cell cycle monitoring, cell proliferation and morphology measurements, and cell biomechanics studies. Quantitative measurements by system 100 may enable objective criteria decision and classification. According to one embodiment, controller 100 may perform one or more processes described herein, including the operations described in FIG. 2. Information generated by quantitative phase measurements of system 100 may provide different information in real time when compared with more traditional microscopy approaches. Measurements performed by system 100 may be noninvasive in that one or more lasers are used to ablate or pull on cellular objects. Through the combination of QPM and laser tweezers, system 100 can provide access to previously inaccessible information about cell morphology function and mechanics. In addition, conventional fluorescence can be integrated into system 100 to provide analysis capabilities of generic fluorescence probes (e.g., GFP).

Controller 120 may be configured to perform one or more processes for real time analysis of changes in cell membranes and cell organelles. Controller 120 may perform operations for analysis of perturbations/alterations and manipulation produced by the laser scissors and/or tweezers of laser system 110. Controller 120 may be configured to control the QPM 105 to determine optical path-length of the sample, measure organelle movement in a cell, and quantify cell dynamics including membrane motility. In one exemplary application, individual cells are killed with the laser scissors and the behavior of adjacent cells are studied using unique features of QPM 105. System 100 is configured for rapid and real-time analysis of changes in membrane activity that allows for the study of activation of wound healing response by cells.

Figure 2:
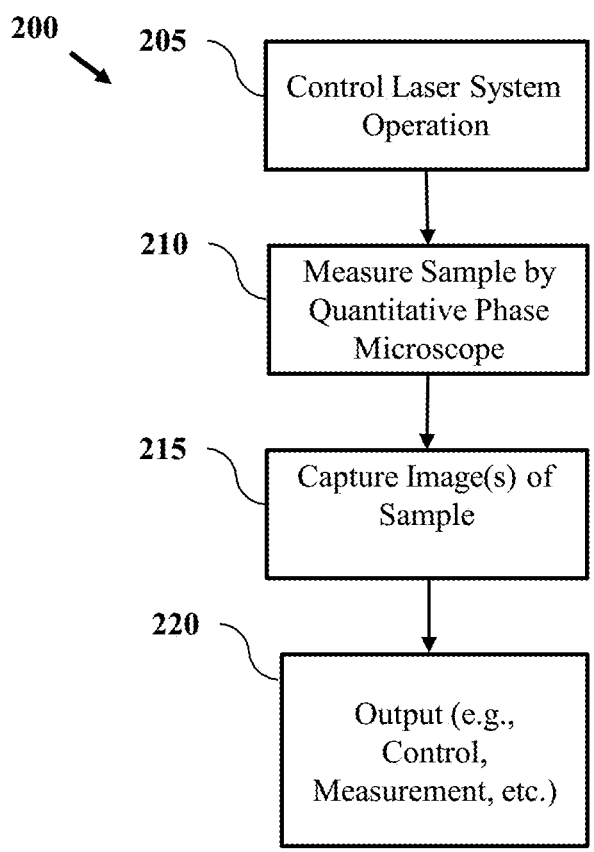
FIG. 2 illustrates a process for operation of a QPM microscope having a laser system according to one or more embodiments.

FIG. 2 illustrates a process for operation of a quantitative phase microscope and laser system according to one or more embodiments. Process 200 may be performed by a device or system of components. Process 200 includes one or more operations which may be performed by a quantitative phase microscope (QPM) system.

Process 200 can include controlling laser system operation at block 205. According to one embodiment, control of laser system operation may include performing at least one of a laser scissors and laser tweezers operations on a sample. The laser tweezers operation may allow for selection and or trapping of a cell or cellular organism. The laser scissors may allow for ablation/alteration of one or more cells or cellular components. In certain embodiments, the laser system is configured to output a shockwave to the sample to simulate trauma to one or more cellular structures and organelles.

At block 210, a QPM may be controlled to image a sample and effects of the laser system may be imaged. The effects may be image and analyzed by a quantitative phase microscope (QPM). The QPM (e.g., QPM 105) may be configured to image a sample for a period of time. According to one embodiment, the process for imaging a sample includes use of a semi-reflective coverslip. Images of the sample may be captured at block 215 for analysis. By combining a QPM and laser system, cellular processes may be observed and responses to the laser system may be analyzed. According to one embodiment, process 200 may optionally include outputting control signals at block 220. Control signals output at optional block 220 may be for control of a QPM and/or laser system. In other embodiments, output at optional block 220 may include images and analysis of at least one astrocyte of the sample. Optional output at block 220 can include measurements by a QPM of at least one of recovery of the sample, intracellular dynamics, and quantitative changes in membrane thickness in real time.

According to one embodiment, a QPM may be controlled at block 210 to measure at least one of recovery of the sample, intracellular dynamics, and quantitative changes in membrane thickness in real time. Determinations at block 210 can include optical path-length of the sample, measurement of organelle movement in a cell, and quantifying cell dynamics including membrane motility. The QPM can also measure at block 210 a repair process in a sample introduced with at least one pharmaceutical. Measurement at block 210 can also include imaging a cell and determining changes in cell thickness and a resolution of intracellular cytoplasmic damage.

Figure 3:
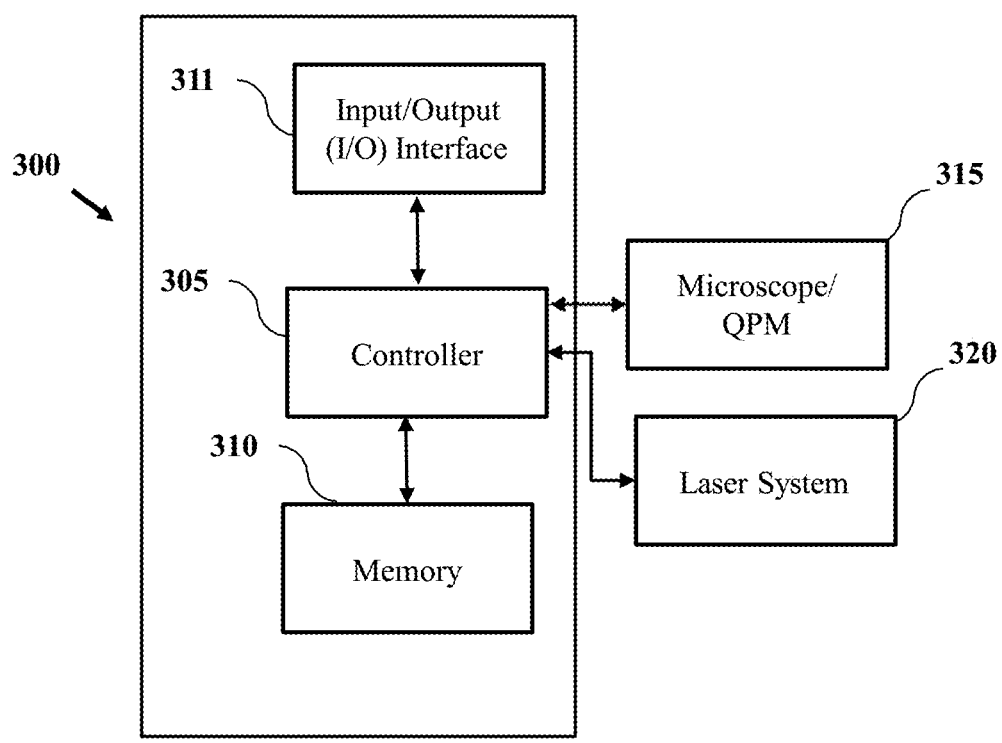
FIG. 3 depicts a device configuration according to one or more embodiments.

FIG. 3 depicts a device configuration according to one or more embodiments. According to one embodiment, a controller may be configured to interoperate with a QPM and a Laser System. FIG. 3 illustrates device 300 including controller 305 and memory 310. Controller maybe configured to output control signals and receive data from one or more of microscope/QPM 315 and laser system 320. Device 300 may optionally include input/output (I/O interface block 311 to interface with a user and/or external devices.

Astrocytes Analysis after Traumatic Brain Injury (TBI) Using Quantitative Phase Microscopy Systems and methods are described herein to perform quantitative phase imaging of astrocyte cells before, during, and after exposure by a laser-induced shockwave (LIS). As an initial step to investigate TBI at the cellular level, embodiments are directed to capturing 3D images of a LIS injury and quantitatively measure the changes in the cell membrane, as well as internal cell structure.

Traumatic brain injury (TBI) can result from external force causing injury to the brain. Astrocytes are the most numerous cells in the central nervous system and have been shown to play a role in detecting, remodeling, and repairing the nervous tissue after a brain injury. However, the exact functional role of astrocytes after TBI is still a matter of debate. To further investigate the mechanism of the TBI and recovery, embodiments are directed to systems that enable studying the functional role of astrocytes after TBI. As a simulation for the trauma at the cellular level, embodiments include using a nanosecond laser-induced shockwave (LIS) to create a precise controllable mechanical force in the medium at a controlled distance from astrocytes. Previously, it has been difficult to effectively measure the cellular changes after LIS. Embodiments include use of a Quantitative Phase Microscope (QPM) to enable monitoring the cells during the shockwave injury and afterwards. This system enables the measurement of the damage and recovery processes of the cells, intracellular dynamics, and quantitative changes in the membrane thickness in real time. In certain embodiments, fluorescent microscopy can be added to the system to localize and quantify changes in calcium and other molecular components during and after shockwave injury, thus providing a unique combination of imaging modalities to study TBI as well as laser-induced trauma in other cellular model systems.

For analysis of trauma to cells, embodiments are discussed herein that include quantitative phase imaging (QPI) to study extreme transparent cells and tissues without the photo-bleaching often encountered when fluorescent probes are used. This modality uses interferometry and precisely quantifies the optical path-length caused by the sample, enabling the ability to image transparent features in cells, measure the movements of their organelle, and quantify the cell dynamics including membrane structure and motility.

Laser-Induced Shockwave (LIS)

If a fluid is irradiated by laser light with an irradiance beyond its optical breakdown threshold, the nonlinear absorption leads to photo-ionization and then, plasma formation. The difference in the pressure and temperature of the plasma and the fluid will cause the plasma to expand creating a cavitation bubble. The bubble expansion causes a shockwave, propagating several hundred microns in the fluid. This phenomenon can be used as a way to expose cells to damage that is caused by the mechanical force of the shockwave.

The pressure gradient as the function of the distance from the center of the shockwave can been measured, leading to the knowledge of exact pressure the cells are exposed to depending on their relative location to the center of the shockwave.

Quantitative Phase Microscopy

Imaging of living cells is challenging without using labeling techniques due to cell transparency and minimal absorption or scattering light by a cell. However, valuable information may be extracted from the phase changes of light as it interacts with the cells. In this regard, Quantitative Phase-Contrast Microscopy allows for studying the cell morphology as it can measure the surface fluctuations of the cell with the resolution of nanometers.

Figure 4A:
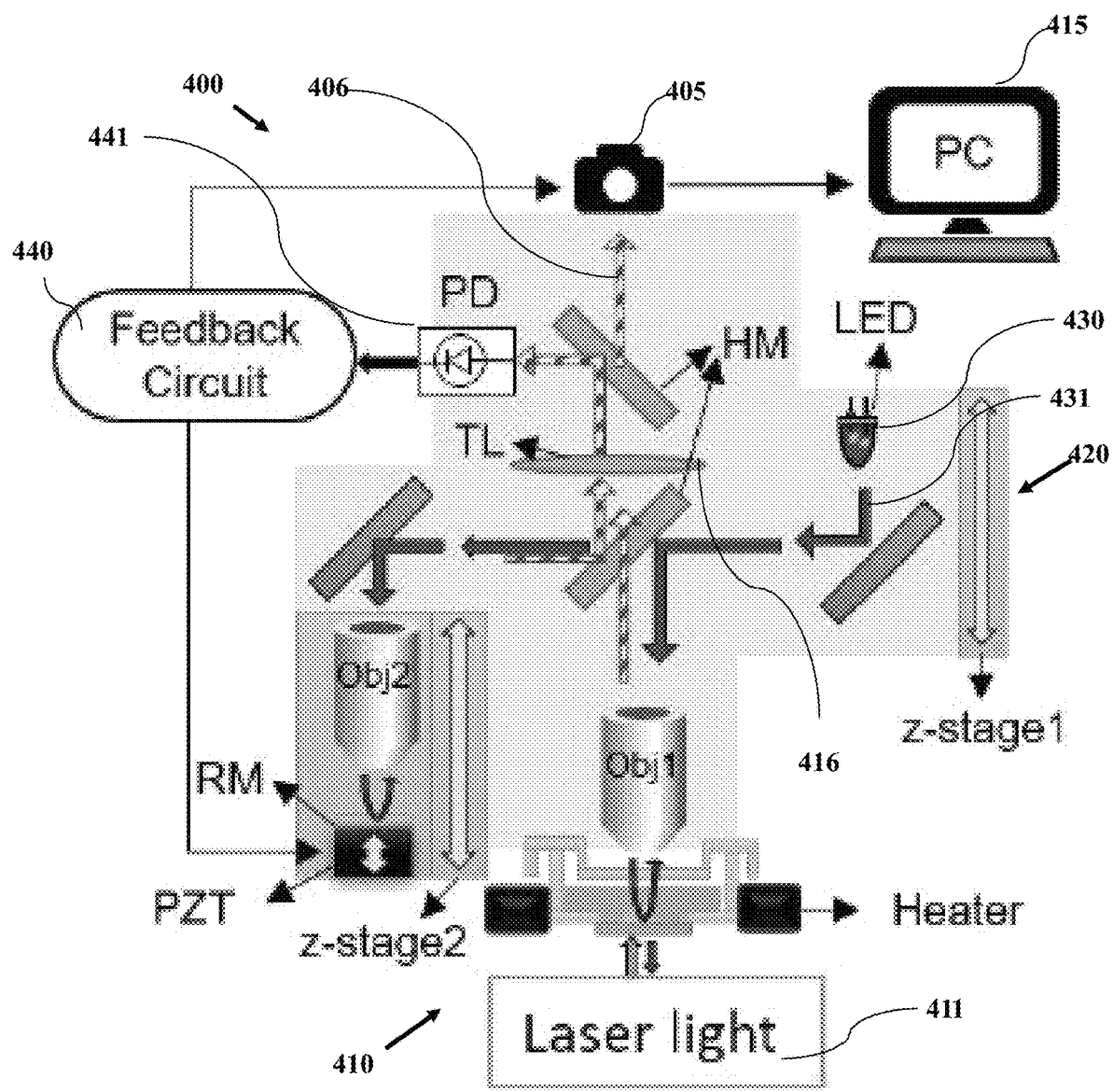
FIGS. 4A-4B illustrate graphical representations of system configurations according to one or more embodiments.
Figure 4B:
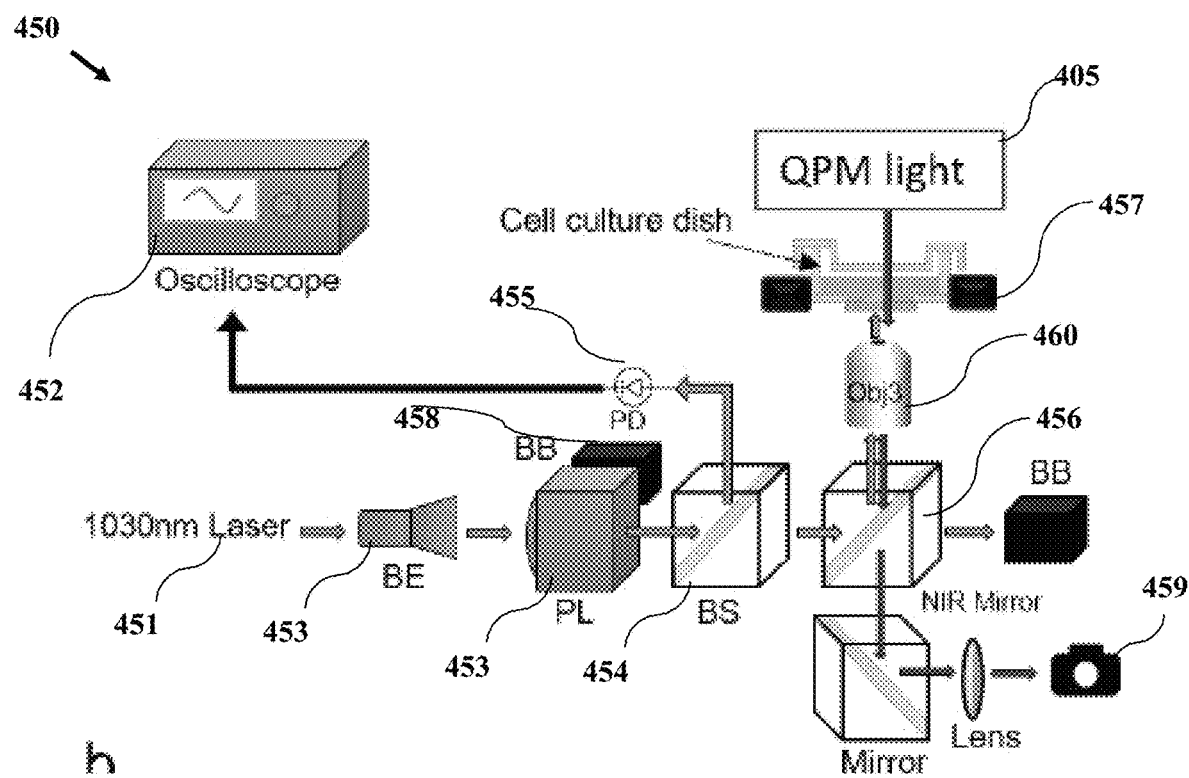

FIGS. 4A-4B illustrate graphical representations of system configurations according to one or more embodiments. FIG. 4A illustrates system 400 including a quantitative phase microscope (QPM) configuration according to one or more embodiments. System 400 includes imaging device/camera 405, laser system 410, and computing device 415. System 400 may operate to analyze and image a sample retained by support structure 420 having dichroic plate 416.

According to one embodiment, system 400 is configured for optical output of light with the center wavelength of $\lambda_c$ to pass through an interferometer, which divides into two beams: one passes through the sample, while the other one is used as the reference beam. Both are reflected on a CCD camera for interferogram acquisitions. According to one embodiment, a quarter-wavelength phase shifting algorithm may be used to calculate the phase image. The optical path-length is periodically shifted by $\lambda_c/4$ resulting in 7 interference images.

$$\theta = \tan^{-1}\left(\frac{I_{(-\frac{3\pi}{2})} \cdots 3I_{(-\frac{\pi}{2})} + 3I_{(\frac{\pi}{2})} - I_{(\frac{3\pi}{2})}}{2(-I_{(-\pi)} + 2I_{(0)} - I_{(\pi)})}\right)$$

Based on the phase, the optical height (OH) is measured as follows $$OH = \frac{\lambda_c}{2\pi} \times \frac{\theta}{2}$$

The real height (RH) of the cells is related to the optical height (OH) with the estimation of mean refractive index of the cells ($n_{cell}$ 1:37) and the medium ($n_{medium}$ 1:337) based on the equation:

$$RH = \frac{OH}{\bar{n}_{cell} - n_{medium}}$$

Laser system 410 includes laser light source 411 having objective lenses (Obj1-2), reference mirror (RM), half mirror (HM) and tube lens (TL). System 400 includes light emitting diode (LED) 430 outputting optical signals 431. Laser system 410 includes laser light source 411 having objective lenses (Obj1-2), reference mirror (RM), half mirror (HM) and tube lens (TL). System 400 includes light emitting diode (LED) 430 outputting optical signals 431. According to one embodiment, system 400 includes a QPM setup based on the Linnik interferometry, including of two identical objective lenses OBj1,Obj2 (e.g., PLN 20X, Olympus) for 20× magnification. In certain embodiments, the system may include two identical water-immersion objective lenses (LUMPLFL 40×, Olympus) for 40× magnification. For interference image acquisition, light is emitted from a red light LED ($\lambda$=633 nm) through a Linnik interferometer; it reflects from the sample and the reference mirror and is focused onto the 12-bit CCD camera 405 (acA1920-40 um, Basler ace) with the maximum frame rate of 41 fps. The camera data is sent to a computing device/PC 415 (Processor core i7, 3.40 GHz) for phase unwrapping analysis.

System 440 also has a feedback control system (feedback circuit 440) to adjust the optical Path Difference (OPD) with the high resolution, including a photodetector and piezoelectric transducer 441. The PZT on the reference arm can adjust the OPD with high resolution (<1 nm) with the maximum variation of 440 nm, at a frequency of about 500 Hz Cells are cultured on hand-made mirror button dishes (D=3:5 cm). The mirror is AR coated for both bandwidth of 550-950 nm and also 1.3 μm to enhance the reflectance of these wavelengths The imaging dish is placed on a heating chamber connected to a Digital Temperature Controller (E5CC, OMRON), to keep the cell medium temperature at 39° C. The reflected beams are shown including a pattern in FIG. 4A.

Shockwave Setup

FIG. 4 B illustrate a shock wave setup according to one or more embodiments. As used herein, a shock wave setup may relate to use of a laser and/or laser system on a sample to simulate and/or impart trauma on a cell or cellular component. System 450 may be used in conjunction with system 400 of FIG. 4A. System 450 includes Q-switched diode-pumped solid-state (DPSS) laser 451 (Flare NX, Coherent, Santa Clara, Calif.) producing pulses of 1:5±0:2 ns a λ=1030 nm is used to generate shockwaves. The laser pulses can be generated with the frequency up to 2000 Hz. To generate laser pulses, the device is connected to a function generator (GFG-8015G, GWInstek), that can produce 5 v square wave with 0.2-2 MHz. The pulses can be generated with a 120-micro second delay with each trigger of the function generator. The laser beam passes a beam expander 453 and is guided through a half-wave plate polarizer 454 for controlling the laser power. The beam then passes through a beam splitter 454, that directs a portion of the beam into a photodiode 455 for laser power measurement. The output of the photodiode 455 is connected to a 500 MHz, 2 channel digital oscilloscope 452. The rest of the beam is reflected by a NIR mirror 456 and is focused on the cell culture medium 457 from the bottom via a 40× water immersion objective lens (C Achroplan NIR 40×/0.80 W, Zeiss). According to one embodiment, system 450 includes a coverslip for cell culture medium 457 that is at least partially reflecting, and QPM 105 may also include an objective lens located below the sample.

Also, for measuring the laser power entering the objective lens, a photodiode power sensor 458, connected to a power and energy meter console, can be placed in the beam path. For focusing the laser light on the cell medium, another camera 459 is placed under the dish to capture the image of the sample using the same objective 460 that focuses the laser light. The light from the QPM 405 passes through the medium, and since the reflecting mirror is not 100% reflective, a portion of the light passes through the sample and the objective and finally is focused with a converging lens, on a camera.

According to embodiments, a setup for system 450 may utilize pulse energy as $7.5 \times 10^{-5}$ J, the input power as 0.1132 W, and the optical power per unit area at the focus as $$2:68 \times 10^8 \frac{W}{m^2}.$$

It should be appreciated that system 450, and other configurations described herein may utilize other laser configurations.

Cell Preparation

Certain embodiments may include preparation of samples for QPM imaging. In one exemplary embodiment, cortical brain tissue was acquired for experimental testing. Primary astrocytes from the cortex of mice were dissociated by an 8-minute incubation with 2 mg/mL papain (Sigma) in Hibernate E (without Calcium and B27, BrainBits). Astrocytes were re-suspended in Co-culture media (BrainBits) and seeded onto Matrigel-coated glass-bottomed dishes.

Image Acquisition

According to one embodiment, image acquisition can occur in two modes. In a first mode, or normal mode, which has the resolution of 1920×1200 with the maximum frame rate and the fast mode with the maximum frame rate of around (38/4) fps and the resolution of 720×720.

Experimental Results

Embodiments herein describe a method to simulate blast traumatic brain injury in live cells. Processes enable the study of astrocyte response to an injury caused by a shockwave similar to what likely happens in tissue in vivo. Embodiment and processes described herein are promising for several reasons. Firstly, QPM allows high-resolution images of the cells. Changes in membrane dynamics, as well as changes in the thickness and structure of the nucleus and cytoplasm, can be measured quantitatively. Specifically, in the cells in FIG. 7 clearly show LIS generated changes in cell thickness as well as a resolution of intracellular cytoplasmic damage. Secondly, cells can be imaged simultaneously with the application of a shockwave. Cellular changes can be captured right after the shockwave, the only limitation being the frame rate of the camera. Third, the only limitation on how long the cells can be imaged is the computer memory capacity. In other words, cells can be imaged from any period before the shockwave, continuously to any desired period after the shockwave allowing studies on cellular repair over extended periods. Since no dyes or fluorescent probes are used for cell imaging, photo-bleaching is not of concern. Also, a heated cell culture chamber ensures the cells remain relatively healthy. Embodiments described herein can be used to evaluate a repair process including the introduction of different drugs or chemicals that may accelerate healing or even mitigate the damage effects of laser operations. As such, the QPM system may provide a pharma screening system. By way of example, the QPM may be controlled to measure the repair process, including one or more sample characteristics described herein, in a sample introduced with at least one pharmaceutical.

The system described here is capable of capturing Quantitative phase images, Phase-Contrast images, and also fluorescent images. With respect to fluorescent images, we will be able to correlate different protein signaling with the changes in the membrane, cytoplasmic, and nucleus dynamics in response to the injury. Modulating drugs or agents may then be applied in an effort to improve the healing processes or mitigate the damage produced.

Figure 5A:
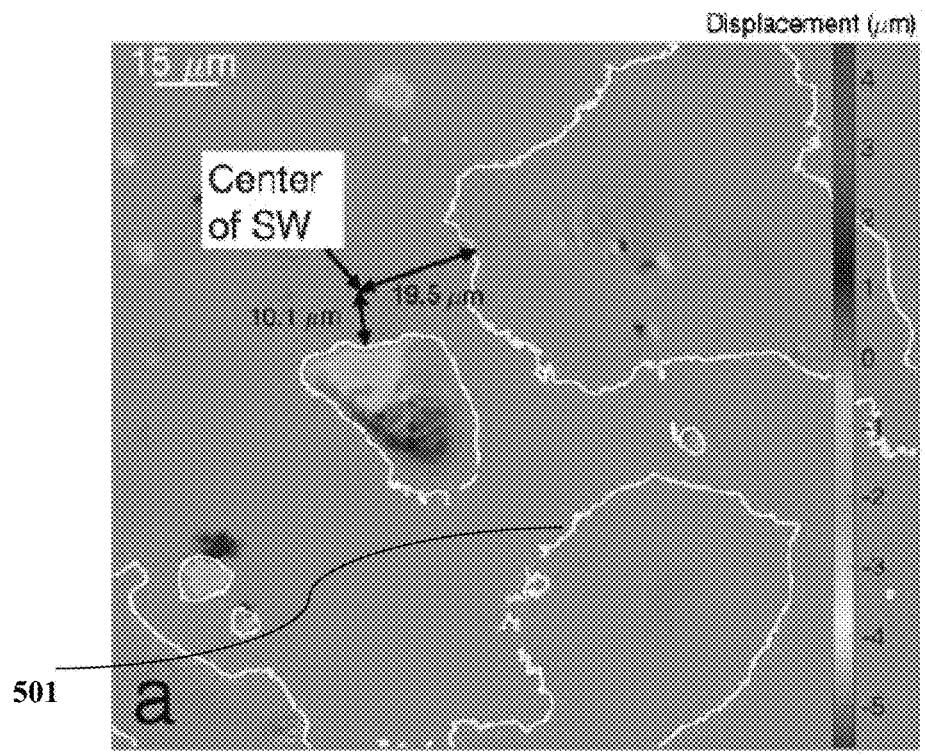
FIGS. 5A-5B illustrate graphical representations of quantitative phase measurements according to one or more embodiments.
Figure 5B:
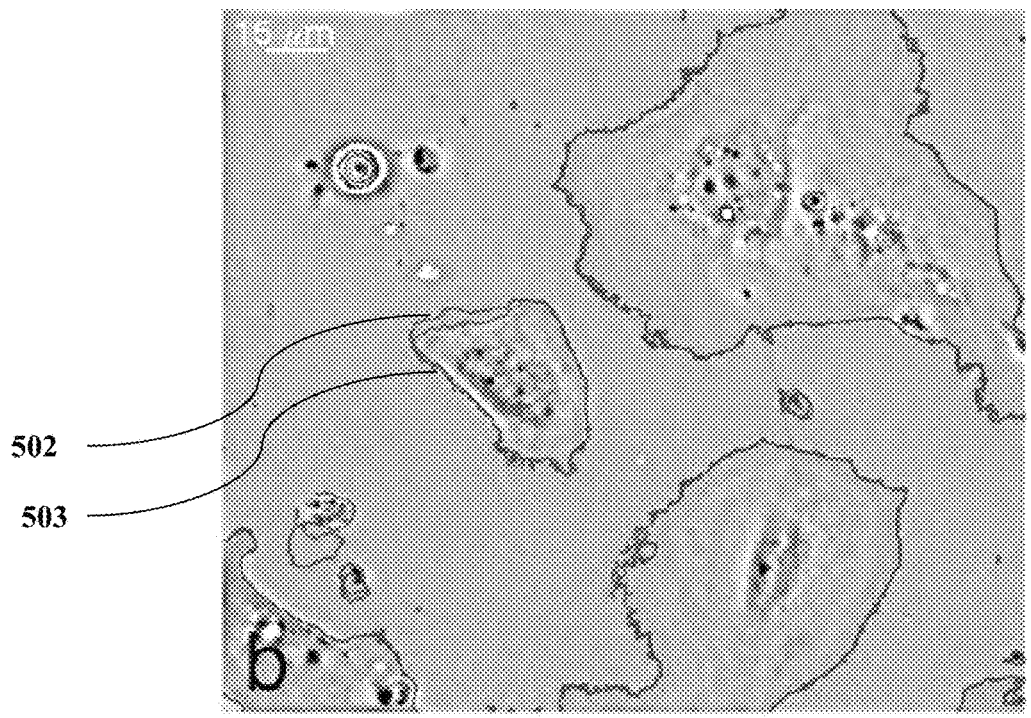

FIGS. 5A-5B illustrate graphical representations of quantitative phase measurements according to one or more embodiments. According to one embodiment, the microscope can acquire phase contrast (PhC) and quantitative phase images simultaneously, and displacements caused by the shockwave in x, y and z directions are measured. The displacements in x-y can be measured using PhC images and in z can be measured with QPM images. In this regard, two images (before and after the shockwave) were chosen as examples for FIGS. 5A-5B. The time difference between the two images was 0.3 second. FIGS. 5A-5B illustrate a displacement image and phase contract (PhC) image of the same field of view. FIG. 5A shows the displacement in cells caused by the shockwave. A flow away from the center of the shockwave in the nearest cell, and only small changes in nucleus of the farther cells can be seen. The cell boundaries before the shockwave has been shown by 501. Displacement of cells from 1.2 s to 41 s after the 2nd shockwave. The center of the shockwave is shown with a white star in FIG. 5A. FIG. 5B is a PhC image of the cells after shockwave. The boundaries of the cells before the shockwave has been shown by 502, and the boundaries for the current image has been shown by lines 503.

The changes in the z-direction may be obtained by calculating the real height, for each image and taking the difference between the height values of the QPM images before and after the shockwave. Looking at the cell, located 10.1 μm away from the center of the shockwave, a deformation of the cell occurs. A decrease in the height at a maximum of 1.65 μm, to an increase at a maximum of 1.47 μm can be seen as we move away from the center of the shockwave. Despite these significant changes close to the shockwave epicenter, only a small amount of height change in other cells in the field of view can be seen FIG. 5A. In the PhC image FIG. 5B the membrane borders of the cells before and after the shockwave are illustrated, respectively. Although the membrane displacement of the cells can be observed, the changes in the height of the cell cannot be measured quantitatively using PhC imaging. To further assess the system, a second shockwave was applied at the same location as the first one.

Figure 6:
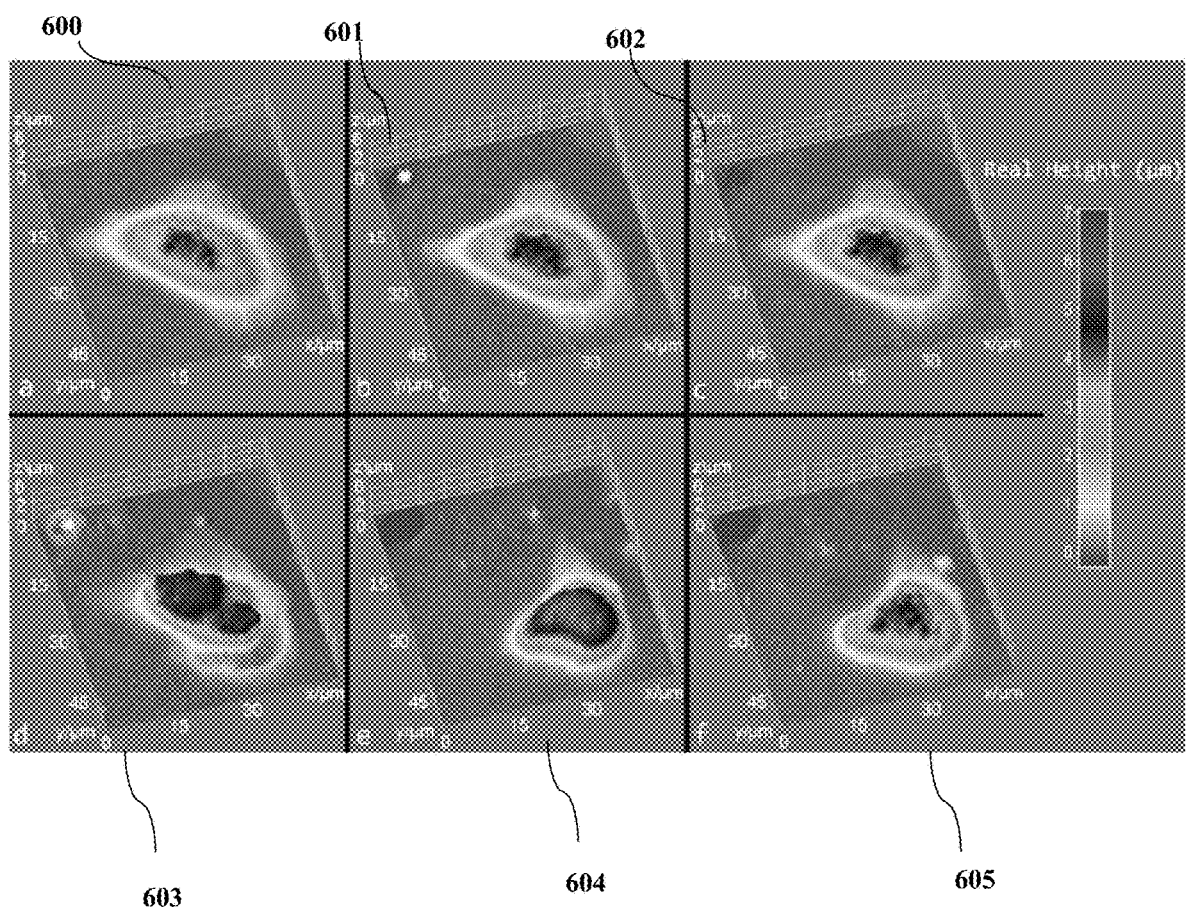
FIG. 6 illustrates constructed images of a cell according to one or more embodiments.

FIG. 6 illustrates constructed images of a cell according to one or more embodiments. According to one embodiment, a system as described here with a QPM may be configured to constructed 3D images 600, 601, 602, 603, 604, and 605 of the cell with the 10.1 micron distance from the center of the shockwave (SW). In FIG. 6, portion 600 (e.g., element a) illustrates the cell before a SW, portion illustrates the cell during a 1st SW, portion 602 (e.g., element c) illustrates 1.2 s after the 1st SW/before a 2nd SW, portion 603 (e.g., element d) illustrates during a 2nd SW, portion 604 (e.g., element e) illustrates 1.2 s after the second SW, and portion 605 (e.g., element f) illustrates 41 s after 2nd SW. FIG. 6 shows how the second shockwave affected the nearest cell. This system captures how this cell has been displaced during the shockwave in 3D (portion (d)). Furthermore, portions 604 (e.g., element e) and 605 (e.g., element f) clearly display how this cell has changed shape over 40 seconds. Though no distinctive internal cellular changes are seen in the QPM images following the first shockwave, following the second shockwave considerable changes are observed in the nucleus (center) region of the cell.

Figure 7:
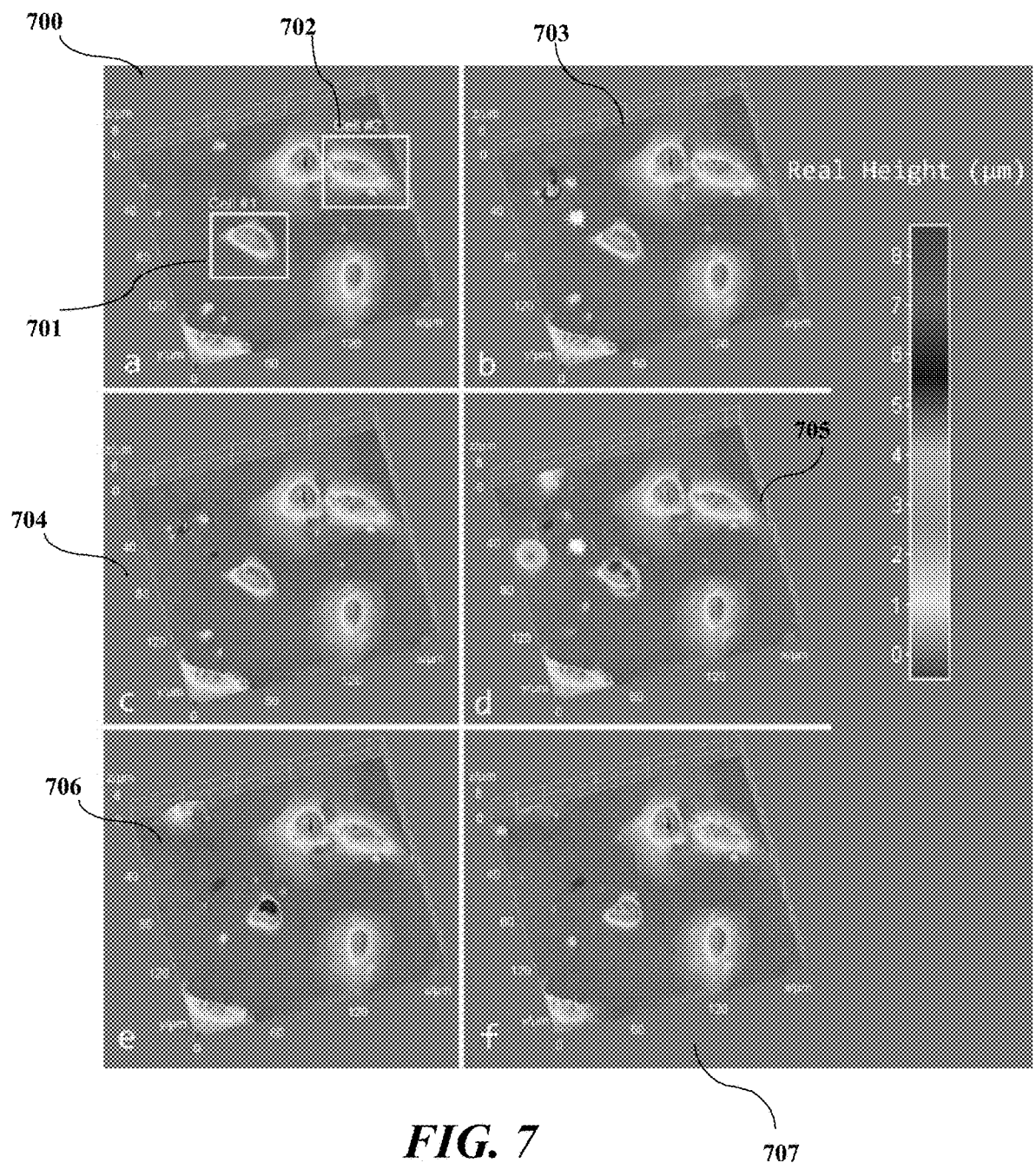
FIG. 7 illustrates constructed images of a cell according to one or more other embodiments.

FIG. 7 illustrates constructed images of a cell according to one or more embodiments. FIG. 7 displays a series of constructed 3D images 700, 703, 704, 705, 706 and 707 of the whole field of view encompassing the pre and post LIS effects for the first shockwave, and following the second shockwave. In FIG. 7, constructed 3D images of the cells in the field of view are shown in portion 700 (e.g., element a) before a shockwave (SW), portion 703 (e.g., element b) during 1st SW, portion 704 (e.g., element c) 1.2 s after 1st SW/before 2nd SW, portion 705 (e.g., element d) during 2nd SW, portion (e) 1.2 s after SW and portion 706 (e.g., element f) 41 s after 2nd SW. In this series, little or no effects of LIS are detected after the first shockwave, but after the second shockwave, considerable effects are noticed not only in the central cell (labelled cell #1—701) closest to the shockwave initiation point but also in the nucleus and cytoplasm of the cell above (labelled cell #2—702). In this cell, there are distinct changes in the cytoplasm that appear as granulation or fragmentation of cellular components.

Figure 8:
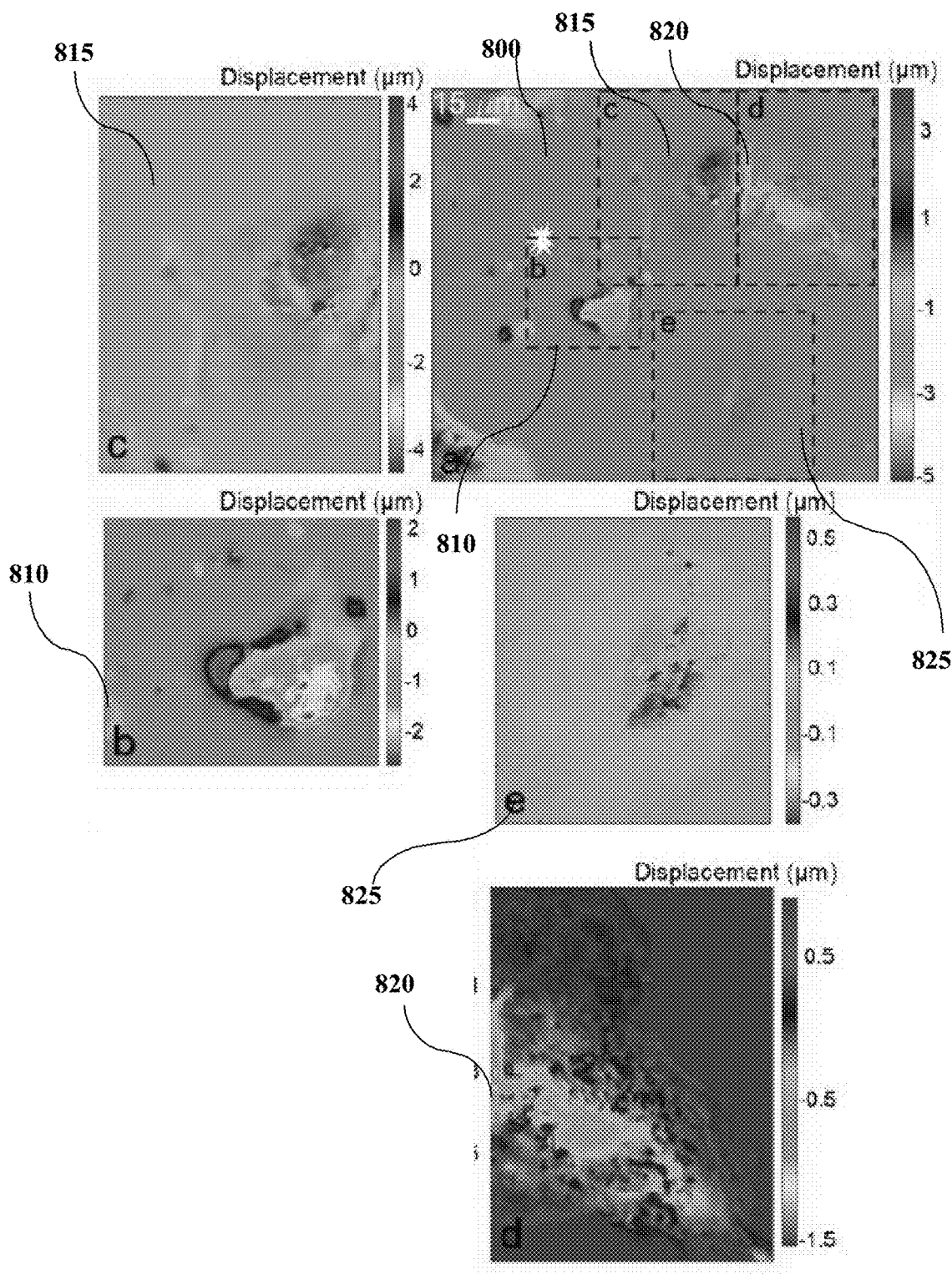
FIG. 8 illustrates a series of constructed images of a cell according to one or more embodiments.

FIG. 8 illustrates a series of constructed images of a cell according to one or more embodiments. FIG. 8 shows the displacement of the cells 40 s after the second shockwave. The displacement in the whole field of view is shown as 800 in FIG. 8. Portions of view 800 are enlarged and shown as 810, 815, 820 and 825. A slight decrease, approximately 0.2 micrometers, in membrane height of the cell is shown in portion 810 (e.g., element b) is observed, which suggests that this cell may be retracting toward its center. Moreover, even though there are no significant changes in the border of the cell shown in portion 810, changes from 2.5 μm decrease to 2 μm increase in different parts of the cell is measured. The cell in portion 820 (e.g., element d) of FIG. 8 seems to be forming vacuoles or other damaged cytoplasm structures, as there is an approximately 0.5 μm increase in round structures. These structures match very nicely with those seen in the cytoplasm of the same cell in portion 707 (e.g., element f) of FIG. 7.

In conclusion, by integrating Quantitative Phase Microscopy with laser-induced shockwaves, methods are provided to study traumatic brain injury (TBI) at a cellular level. This system allows the application of various degrees of shockwave injury while simultaneously monitors bulk membranes changes, cell shape changes, and real-time analysis of damage and recovery of intracellular damage. This system is also a promising method to study the role of not only the astrocytes in TBI, but also neurons and other astroglial cells. In addition, this method should be useful to study how these different cells interact with each other in response to the shockwave injury in the TBI model as well as in induced trauma in other cellular model systems.

While this disclosure has been particularly shown and described with references to exemplary embodiments thereof, it will be understood by those skilled in the art that various changes in form and details may be made therein without departing from the scope of the claimed embodiments.

What is claimed is:

1. A quantitative phase microscope (QPM) system, the system comprising:
    a structural unit configured to retain a sample, wherein the structural unit includes a dichroic plate;
    a laser system configured to perform a laser scissor operation and laser tweezer operation on the sample; and
    a quantitative phase microscope (QPM) configured to image the sample, wherein the dichroic plate is transparent to the laser system and reflective to output of the QPM.

2. The system of claim 1, wherein the dichroic plates is a substrate for the sample.

3. The system of claim 1, wherein the laser system is configured to output a shockwave output to the sample to simulate trauma in the sample.

4. The system of claim 1, wherein the QPM system is configured to simulate and analyze trauma on at least one of cellular structures and organelles.

5. The system of claim 4, further comprising a fluorescent microscope element configured to localize and quantify at least one molecular component of the sample during and after shockwave injury.

6. The system of claim 1, wherein the laser system is configured to image and analyze at least one astrocyte of the sample.

7. The system of claim 1, wherein wherein the laser tweezer operation is configured for at least one of holding and moving the sample, and wherein the laser scissor operation includes cutting at least one of a cellular component and cellular membrane.

8. The system of claim 1, wherein the QPM is configured to measure at least one of recovery of the sample, intracellular dynamics, and quantitative changes in membrane thickness in real time.

9. The system of claim 1, further comprising a controller configured to:
control the laser system; and
control the QPM, wherein the controller controls the QPM to image the sample.

10. The system of claim 9, wherein the controller is configured to control the QPM to determine optical path-length of the sample, measure organelle movement in a cell, and quantify cell dynamics including membrane motility.

11. A method for operation by a quantitative phase modulated (QPM) system, the method comprising:
controlling, by a controller, a laser system configured to perform a laser scissor operation and laser tweezer operation on a sample; and
controlling, by the controller, imaging by a quantitative phase microscope (QPM) to image the sample, wherein the sample is retained by a structural unit including a dichroic plate, and wherein the dichroic place is transparent to the laser system and reflective to output of the QPM.

12. The method of claim 11, wherein the laser system is configured to output a shockwave output to the sample to simulate trauma in the sample.

13. The method of claim 11, wherein the laser system is configured to simulate and analyze trauma on at least one of cellular structures and organelles.

14. The method of claim 11, further comprising controlling a fluorescent microscope element to localize and quantify at least one molecular component of the sample during and after shockwave injury.

15. The method of claim 11, further comprising controlling the laser system to image and analyze at least one astrocyte of the sample.

16. The method of claim 11, wherein the laser tweezer operation is configured for at least one of holding and moving the sample, and wherein the laser scissor operation includes cutting at least one of a cellular component and cellular membrane.

17. The method of claim 11, further comprising controlling the QPM to measure at least one of recovery of the sample, intracellular dynamics, and quantitative changes in membrane thickness in real time.

18. The method of claim 11, further comprising controlling the QPM to determine optical path-length of the sample, measure organelle movement in a cell, and quantify cell dynamics including membrane motility.

19. The method of claim 11, further comprising controlling the QPM to measure repair process in the sample introduced with at least one pharmaceutical.

20. The system of claim 11, wherein imaging a cell includes determining changes in cell thickness and a resolution of intracellular cytoplasmic damage.

* * * * *